(12) United States Patent
Bourilkov et al.

(10) Patent No.: US 9,189,667 B2
(45) Date of Patent: Nov. 17, 2015

(54) SMART POWER SOURCE

(71) Applicant: The Procter & Gamble Company, Cincinnati, OH (US)

(72) Inventors: Jordan Todorov Bourilkov, Stamford, CT (US); Steven Jeffrey Specht, Bethel, CT (US); Sergio Coronado, Bethel, CT (US); Konstantin Dimitrov Stefanov, Cambridge (GB); Suat Ayoz, Cambridge (GB)

(73) Assignee: The Gillette Company

( * ) Notice: Subject to any disclaimer, the term of this patent is extended or adjusted under 35 U.S.C. 154(b) by 414 days.

(21) Appl. No.: 13/721,735

(22) Filed: Dec. 20, 2012

(65) Prior Publication Data

US 2014/0062663 A1 Mar. 6, 2014

Related U.S. Application Data

(60) Provisional application No. 61/580,379, filed on Dec. 27, 2011.

(51) Int. Cl.
*H04Q 5/22* (2006.01)
*G06K 7/10* (2006.01)
(Continued)

(52) U.S. Cl.
CPC ............ *G06K 7/10366* (2013.01); *A61F 13/42* (2013.01); *A61F 13/84* (2013.01); *G01D 9/005* (2013.01); *G01D 11/305* (2013.01); *G01K 1/024* (2013.01); *G01K 3/04* (2013.01); *G01N 33/48792* (2013.01); *G01V 15/00* (2013.01); *G06K 7/0008* (2013.01); *G06K 7/10178* (2013.01); *G06K 19/077* (2013.01);
(Continued)

(58) Field of Classification Search
CPC ............ G06K 7/10366; G06K 7/0008; G06K 19/0723; G06K 7/10009; G06K 7/10297; G08B 13/2434; G08B 13/2482; G08B 13/246; G08B 13/2462; G08B 13/2402; G08B 13/2417
USPC .................. 340/10.1–10.6, 571, 572.1–572.9
See application file for complete search history.

(56) References Cited

U.S. PATENT DOCUMENTS

| 5,959,568 A * | 9/1999 | Woolley ........................ 342/42 |
| 7,561,050 B2 | 7/2009 | Bhogal et al. |

(Continued)

FOREIGN PATENT DOCUMENTS

| EP | 1 693 807 | 8/2006 |
| WO | WO 95/01062 | 1/1995 |
| WO | WO 2004/107251 | 12/2004 |

OTHER PUBLICATIONS

PCT International Search Report with Written Opinion in corresponding Int'l appln. PCT/US2012//070909 dated Apr. 9, 2013.

*Primary Examiner* — Travis Hunnings
*Assistant Examiner* — Sharmin Akhter
(74) *Attorney, Agent, or Firm* — Leo J. White; Kevin C. Johnson; Steven W. Miller

(57) ABSTRACT

An article having a conductive body, a magnetic diverter, and a communication device is described. The magnetic diverter is positioned on an outer surface of the conductive body. The magnetic diverter covers a substantial portion of the outer surface of the conductive body. A communication device is positioned on the outer surface of the diverter or may be recessed therein. The communication device is capable of signal coupling with a reader.

25 Claims, 22 Drawing Sheets

(51) Int. Cl.
  *G06K 19/07* (2006.01)
  *G01K 1/02* (2006.01)
  *G01V 15/00* (2006.01)
  *G06K 7/00* (2006.01)
  *G06K 19/077* (2006.01)
  *H01Q 1/22* (2006.01)
  *G01N 33/487* (2006.01)
  *G01D 9/00* (2006.01)
  *G01K 3/04* (2006.01)
  *A61F 13/84* (2006.01)
  *A61F 13/42* (2006.01)
  *G01D 11/30* (2006.01)
  *G06Q 30/06* (2012.01)
  *H01Q 7/00* (2006.01)
  *H01Q 9/16* (2006.01)
  *G01N 27/12* (2006.01)
  *G01D 1/14* (2006.01)

(52) U.S. Cl.
  CPC ........ *G06K19/0716* (2013.01); *G06K 19/0717* (2013.01); *G06K 19/0723* (2013.01); *G06K 19/07749* (2013.01); *G06K 19/07773* (2013.01); *G06Q 30/0623* (2013.01); *H01Q 1/2225* (2013.01); *A61F 2013/424* (2013.01); *A61F 2013/8473* (2013.01); *A61F 2013/8479* (2013.01); *A61F 2013/8482* (2013.01); *G01D 1/14* (2013.01); *G01N 27/126* (2013.01); *H01Q 7/00* (2013.01); *H01Q 9/16* (2013.01)

(56) References Cited

U.S. PATENT DOCUMENTS

| | | | |
|---|---|---|---|
| 7,586,416 | B2 | 9/2009 | Ariyoshi et al. |
| 7,606,530 | B1 | 10/2009 | Anderson et al. |
| 7,741,970 | B2 | 6/2010 | Cunningham et al. |
| 2007/0080804 | A1* | 4/2007 | Hirahara et al. ............ 340/572.1 |
| 2008/0206627 | A1* | 8/2008 | Wright ............................ 429/93 |
| 2009/0024309 | A1 | 1/2009 | Crucs |
| 2010/0295943 | A1 | 11/2010 | Cha et al. |

* cited by examiner

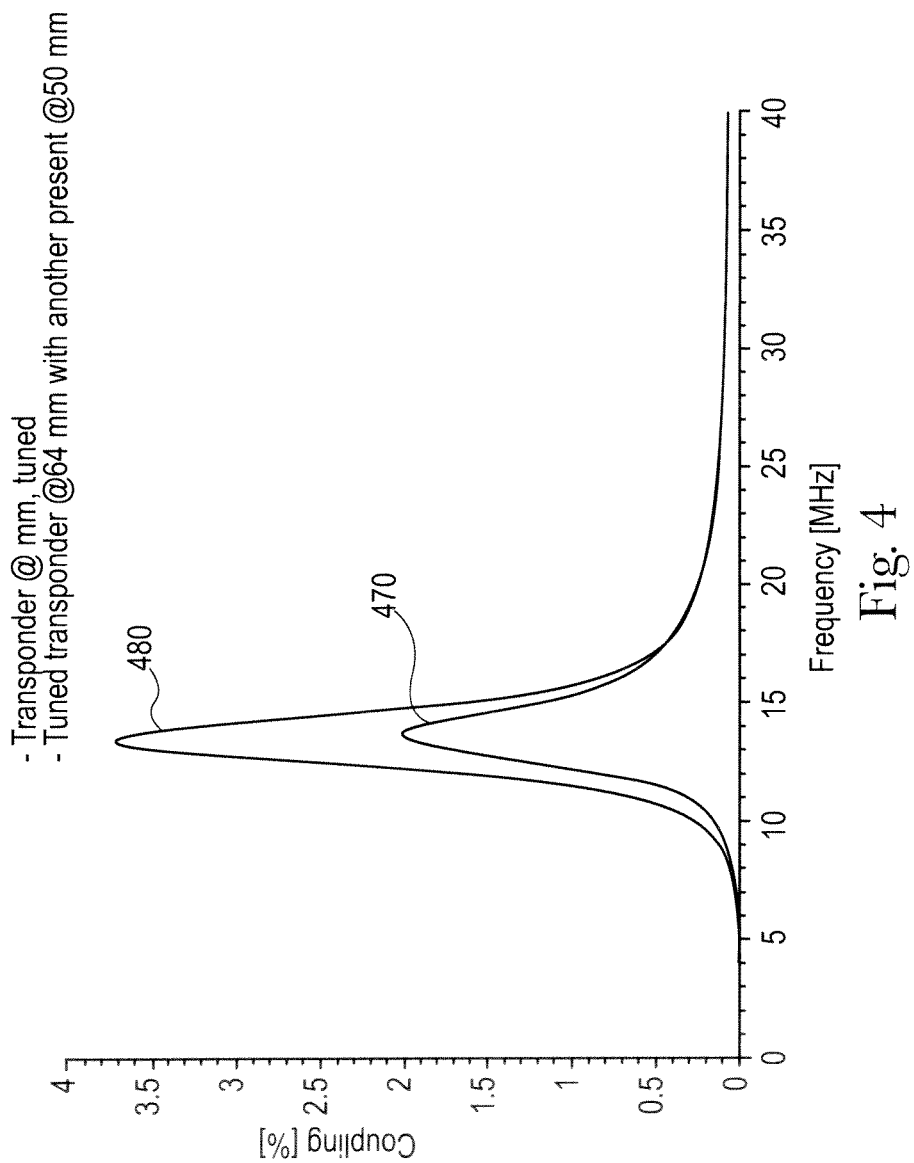

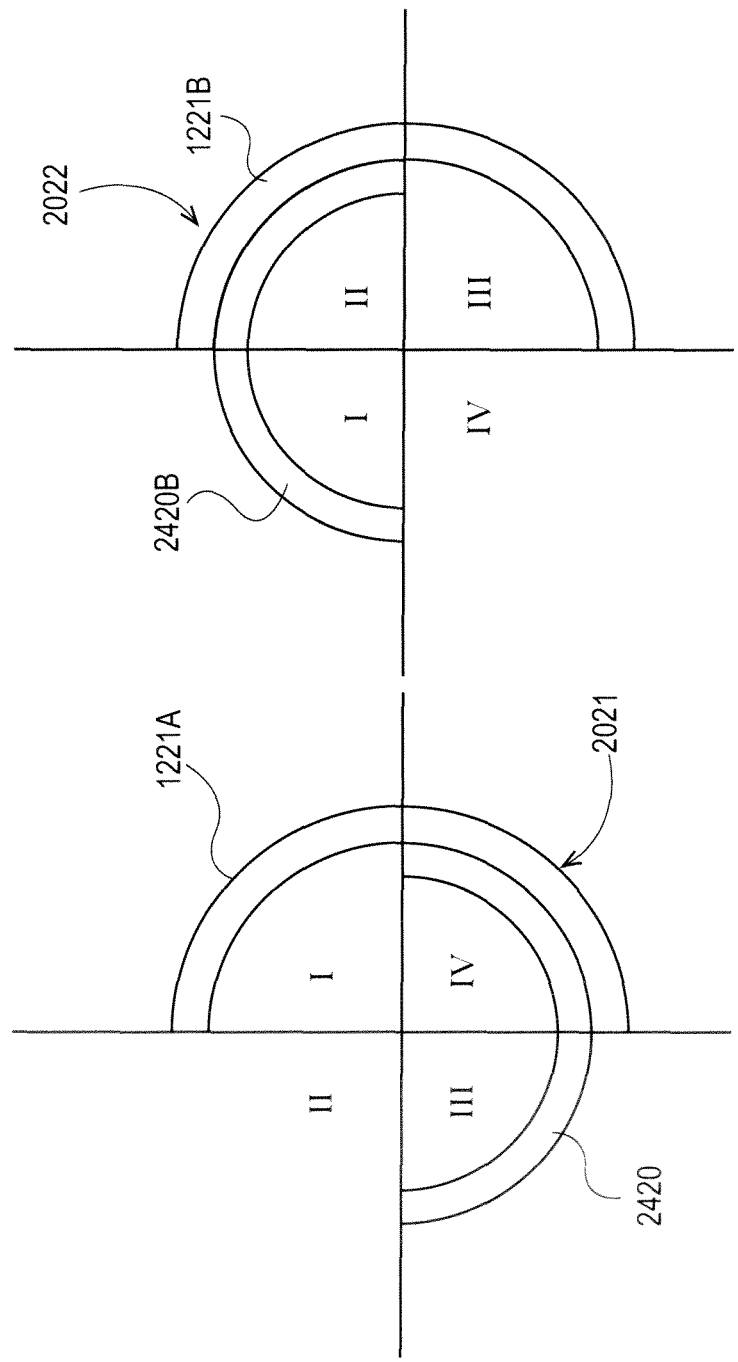

SMART POWER SOURCE

FIELD OF THE INVENTION

The present invention pertains to a portable power supplies and more particularly to batteries.

BACKGROUND OF THE INVENTION

Batteries are utilized in a wide variety of consumer products. While some batteries are rechargeable, others are disposable. Some of the devices that utilize rechargeable batteries provide an indication to the user regarding the remaining energy level of the battery, e.g. cellular phones, MP3 players, powered toothbrushes, etc. However, there are some devices which utilize rechargeable batteries that do not provide an indication to the consumer regarding the remaining energy level. Similarly, devices that utilize disposable batteries generally provide no indication to the consumer regarding the remaining energy level of the disposable battery. For those devices which provide no indication of remaining energy level to the consumer, typically the only indication of low energy levels remaining in the battery (rechargeable or disposable) is in the form of degraded performance of the device. While the consumer could feasibly remove the batteries and test them in a battery tester, this is inconvenient as each battery would have to be removed from the device and tested and then replaced within the device.

As such, there is a need for a device or devices as well as a methodology for allowing a consumer to check the remaining power levels of disposable and/or rechargeable batteries while the batteries are still within the devices which they operate.

SUMMARY OF THE INVENTION

An object having a signal communication device, the object having an outer surface, the object further comprising: an RFID tag positioned on the outer surface of the object, the RFID tag having a resonant frequency and an antenna; and at least one passive repeater having a resonant frequency which is the same as that of the RFID tag, the at least one passive repeater being positioned on the outer surface of the object adjacent to the RFID tag such that signal coupling between the RFID tag and a reader is increased by greater than about 10 percent.

A system comprising a first object and a second object, each of the first object and the second object having an outer surface, the system further comprising: a first RFID tag positioned on the outer surface of the first object, the first RFID tag having a resonant frequency and an antenna; and a second RFID tag positioned on the outer surface of the first object, the second RFID tag having a resonant frequency which is similar to that of the first RFID tag, wherein the first RFID tag and the second RFID tag provide data to a reader, and wherein the second RFID tag is positioned adjacent to the first RFID tag such that signal coupling between the first RFID tag and a reader is increased by greater than about 10 percent.

An electrical component comprising: a body comprising a recess; at least one disposable or rechargeable power source disposed within the recess, the at least one disposable or rechargeable power source comprising an RFID tag positioned on an outer surface of the at least one disposable or rechargeable power source, the RFID tag having a first resonant frequency; a cover capable of engaging the body such that the at least one disposable or rechargeable power source is covered when the cover engages the body; and a passive repeater disposed adjacent the RFID tag, the passive repeater having a second resonant frequency, wherein the first and the second resonant frequencies are similar.

An article comprising: a conductive body; a magnetic diverter positioned on an outer surface of the conductive body, the magnetic diverter covering a substantial portion of the outer surface of the conductive body; and a communication device capable of signal coupling with a reader.

BRIEF DESCRIPTION OF THE DRAWINGS

It is to be understood that both the foregoing general description and the following detailed description describe various embodiments and are intended to provide an overview of framework for understanding the nature and character of the claimed subject matter. The accompanying drawings are included to provide a further understanding of the various embodiments, and are incorporated into and constitute part of this specification. The drawings illustrate various embodiments described herein, and together with the description serve to explain the principles and operations of the claimed subject matter.

FIG. 4 is graphical representation showing a computer simulated model of the signal coupling between a first object and a first reader versus a second object and a second reader including a passive repeater between the second object and the second reader.

FIG. 12B is a schematic view showing a first end view of the communication device and/or antennas of FIG. 12A.

FIG. 12C is a schematic view showing a second end view of the communication device and/or antennas of FIG. 12A.

DETAILED DESCRIPTION OF THE INVENTION

Definitions

Figure 1:
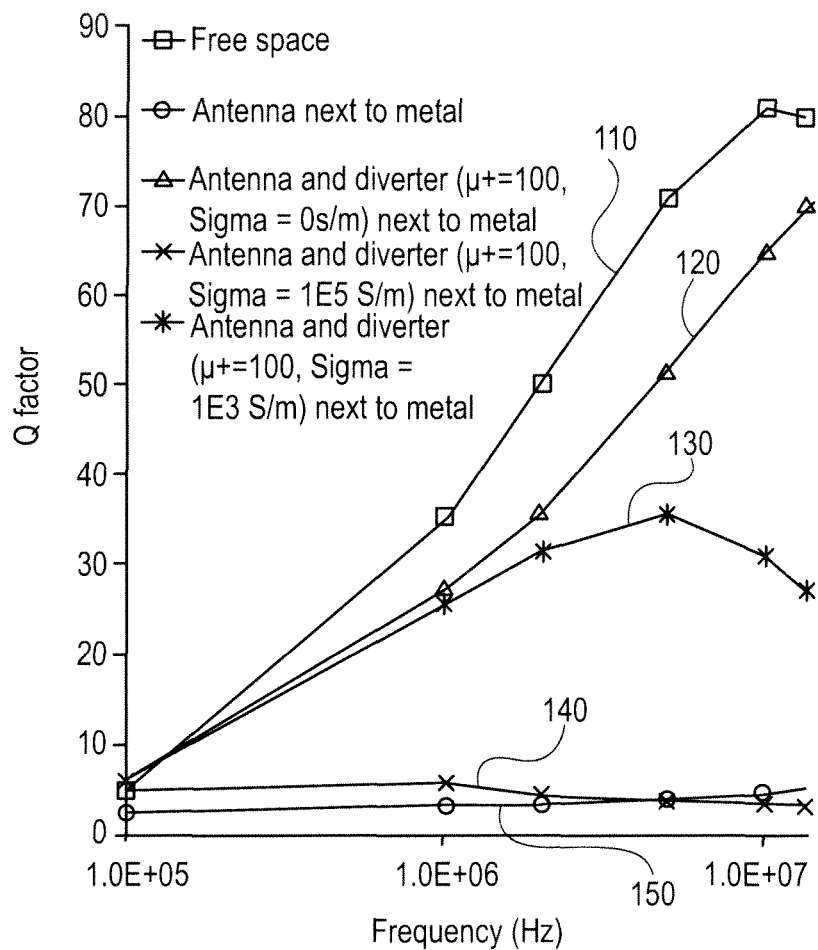
FIG. 1 is a graphical representation showing Q factors for various materials which may be utilized in a diverter.

The following text sets forth a broad description of numerous different embodiments of the present invention. The description is to be construed as exemplary only and does not describe every possible embodiment since describing every possible embodiment would be impractical, if not impossible, and it will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). No term is intended to be essential to the present invention unless so stated. To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

DESCRIPTION

The device of the present invention can promote the communication between an object and a reader. For example, where an RFID tag is utilized, line of sight between the RFID tag and the reader may be beneficial in aiding communication between the RFID tag and a reader. For those objects which may be orientation neutral, the position of the RFID tag may be critical to ensuring that communication may be achieved between the tag and the reader. For example, for a AA battery, the orientation is generally only limited by the position of the positive and negative poles. As such, an RFID tag on the AA battery, in some instances may be positioned such that it is on an opposite side of the battery from the reader. This positioning may reduce the likelihood that the reader and the RFID tag can communicate with one another.

The communication system of the present invention may be utilized on a number of different products. For example, the communication system of the present invention may be utilized on disposable and/or rechargeable batteries. Additionally, other consumer products are contemplated. Some examples include cans of shaving gel, cans of shaving foam, etc. Additionally, the communication system of the present invention may be utilized on devices such as remote control toys and the like. Within the context of disposable or rechargeable batteries, the communication system of the present invention can allow a consumer to receive an indication of the remaining energy level of a disposable and/or rechargeable battery without the removal of the battery from the device which it operates. Additionally, the communication system(s) of the present invention can allow the consumer to receive additional information regarding, for example, an identification number of arbitrary length of the battery or batteries, information about the battery's and/or batteries' state(s), history etc., information about the environment, e.g. temperature, pressure, voltage, current, information about the device in which the batteries are operating or any other analogue information about the device and/or battery or batteries. Additionally, the communication system(s) described herein can by utilized on any cylindrical object and/or any object(s) where omni-directional transmission is desirable.

In some embodiments, the communication system may utilize RFID (radio frequency identification) technology. RFID technology utilizes a radio frequency reader device that transmits an RF (radio frequency) signal at a known frequency. An RFID tag, used in RFID communication, generally comprises an antenna and rectifier. The rectifier converts incoming RF frequency to DC, which powers the RFID tag and other electronic circuitry. The electronic circuitry comprises memory. When powered on, an identification number contained within the memory cells is converted back to an RF signal and transmitted by the antenna to a reader.

The RFID tag may be positioned on and/or contained within an item of interest. In addition to transmitting back the identification number, the tag can also send further information stored in the memory portion of the electronic circuit. Such information may be relevant to further classify the item, obtain more information about the state of the item, history etc.

In addition to information stored in the memory portion, the electronic circuitry may have the ability to convert analogue information about the environment into digital data and transmit the digital data back to the reader. Such digital data could be the temperature, pressure, voltage, current, or any other analogue information about the item that the tag is attached that it is within.

In some embodiments, a transponder may be utilized to transmit information about the remaining energy level in a disposable or re-chargeable battery. This can be done while the disposable or re-chargeable battery is within the device and/or attached thereto.

Where the transponder provides remaining energy levels of a disposable or rechargeable battery, the transponder may comprise a sensor that is capable of measuring battery voltage. The transponder may further comprise an analogue-to-digital converter to convert the measured battery voltage into a binary number having sufficient bit length to achieve sufficient resolution in the voltage measurement. A typical resolution may be 4 bits; however additional bits may be utilized. For example, where accurate sensing is required or desired, a 16 bit length may be used. In contrast, lower resolution may be utilized. For example, 1 bit may be utilized in cases where a yes/no operations or sensing is desired.

The transponder may further comprise a digital memory device to store the converted analogue measurement value as well as the tag identification number and any other relevant data. Moreover, the transponder may further comprise an antenna tuned to the incoming radio frequency of the reader to efficiently receive the incoming RF signal and to transfer an outgoing RF signal having the desired data to the reader.

Reducing Metal Body Attenuation

One of the problems associated with creating a communication device for various products is realized when the communication device is utilized on conductive bodies. Free space radio propagation principles do not apply near highly conductive bodies. Additionally, antenna performance is severely degraded when antennas are placed near metals. As such, simply placing an RFID tag on a battery or on an object with a conductive body may not accomplish the desired effect, e.g. data transfer. Notably, this problem is not limited to rechargeable/disposable batteries. For example, a can of shaving gel, foam, etc. could experience the same issues because of the conductivity of the container. In general, an RFID tag next to metallic body decreases signal coupling between the reader and the tag by 10×.

It has been discovered by the inventors that one way to prevent the effects arising from metal proximity to the antenna is to prevent the electromagnetic field from entering the metal. For example, by placing a material with suitable electromagnetic properties and dimensions between the antenna and the metal surface the electromagnetic field may be diverted around the metallic/conductive body of the product. The properties of the diverter material depend on the exact metal used and the RFID frequency. The magnetic diverter effectively isolates the tag from the can.

FIG. 1 shows estimated quality factors, a number suitable for characterizing the performance of RFID tags, as a function of the frequency between 100 kHz and 20 MHz for different electromagnetic parameters of the magnetic material, and the metal being mild steel. A high quality factor generally corresponds to higher induced voltage in the antenna of the RFID tag and better reading range.

As shown, the best estimated diversion material is free space (represented by curve 110) which achieves the highest quality factor over all. However, this proposition is unrealistic as generally space constraints exist. For the curves 120, 130, and 140, the variable $\mu$ is the magnetic permeability and the variable $\delta$ (sigma) is the electrical conductivity in Siemens per meter. The overall trend of FIG. 1 shows that for a given $\mu$, diverter materials having a lower electrical conductivity interfere less with signal coupling between a communication device and a reader.

The magnetic material would divert the electromagnetic field away from the metal object if its magnetic permeability is much higher than the permeability of the metal. And, accordingly, the eddy currents and losses in the metal would be much reduced, and the induced voltage in the antenna would increase. Due to this function the magnetic material is called "magnetic diverter". The high permeability of the magnetic diverter increases the inductance of the antenna and reduces the resonant frequency of the tag front end. But, this can be easily compensated for by designing the antenna taking into account the magnetic properties of the diverter, or by reducing the value of the parallel capacitance in the front end LC circuit. It has been established that $\mu$>100 values assure good performance.

The electric conductivity of the material of the magnetic diverter has to be much lower than that of metals. This is typically realized by using ferrite-based materials. For common mild steel the relative magnetic permeability of the diverter should be above 100. The thickness of the magnetic diverter would depend on the magnetic permeability, and thicknesses below 100 µm are possible. In the context of disposable or rechargeable batteries, the thickness of the diverter may be constrained such that the overall dimensions of the battery including the diverter are the same sizes as the standard sizes currently utilized.

Figure 2A:
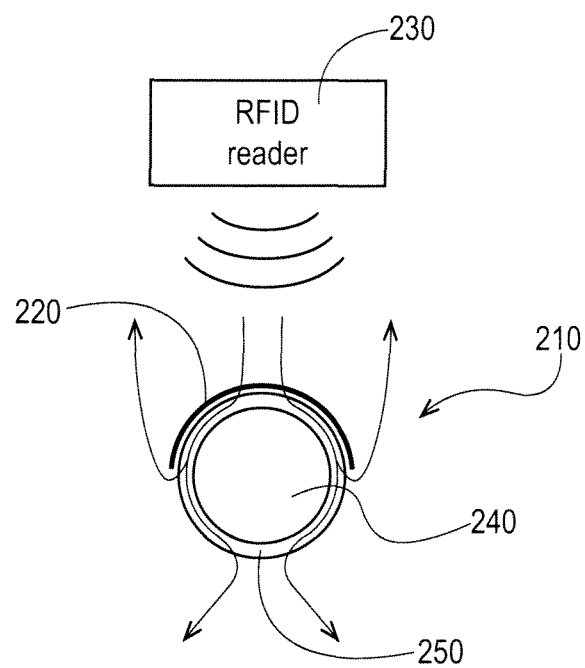
FIGS. 2A-2D are schematic views showing a variety of configurations regarding objects and a reader, where the objects include a magnetic diverter.

As shown in FIGS. 2A-2D, an article 210 is shown comprising a conductive body 240, a magnetic diverter 250, and a communication device 220, e.g. RFID tag. There are several different arrangements possible regarding the communication device 220 and the magnetic diverter 250 disposed on the article 210. In some embodiments, the diverter 250 may be placed under the communication device 220, covering area equal or greater than the area of the communication device 220. In some embodiments, a diverter 250 may completely surround the conductive body 240. As shown in FIG. 2A, the article 210 may be oriented such that the communication device 220 is positioned adjacent a reader 230.

Figure 2B:
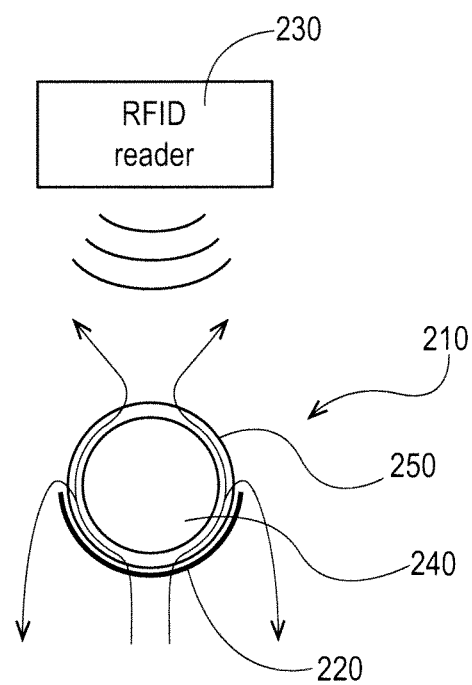

As shown in FIG. 2B, it is believed that the article 210 may be positioned such that the communication device 220 is disposed opposite the reader 230 and still provide a sufficient signal coupling—provided of course that the magnetic diverter 250 is utilized.

Figure 2C:
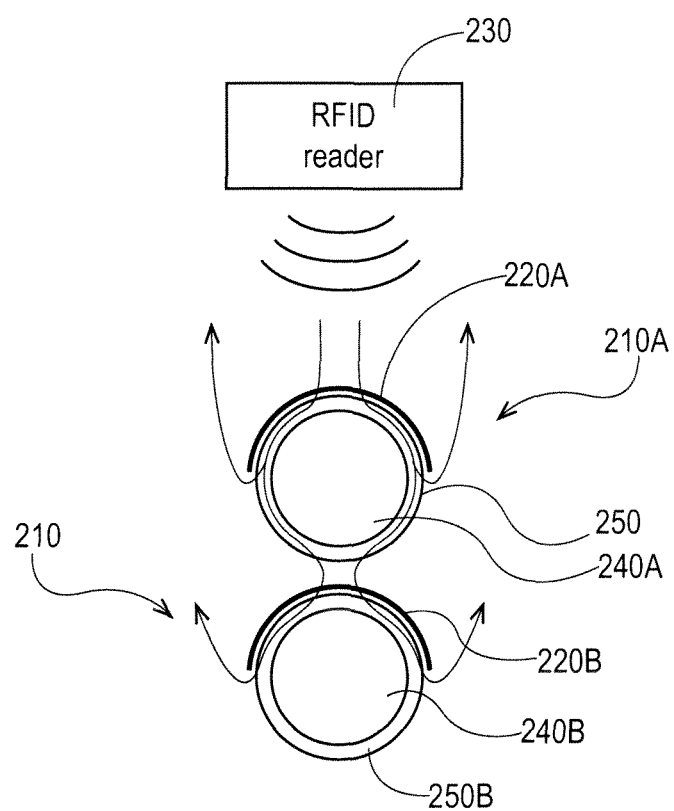

As shown in FIG. 2C, it is believed that an array of articles 210A and 210B may be arranged such that sufficient signal coupling can occur between the reader 230 and a first communication device 220A and/or a second communication device 220B. As shown, the articles 210A and 210B may be constructed as described heretofore with regard to the article 210. Namely, the first article 210A may comprise a conductive body 240A, a magnetic diverter 250A, and the first communication device 220A. Similarly, the second article 210B may comprise a conductive body 240B, a magnetic diverter 250B, and the second communication device 220B. As shown, the second article 210B may be oriented such that the second communication device 220B is positioned immediately adjacent to the first article 210A.

Figure 2D:
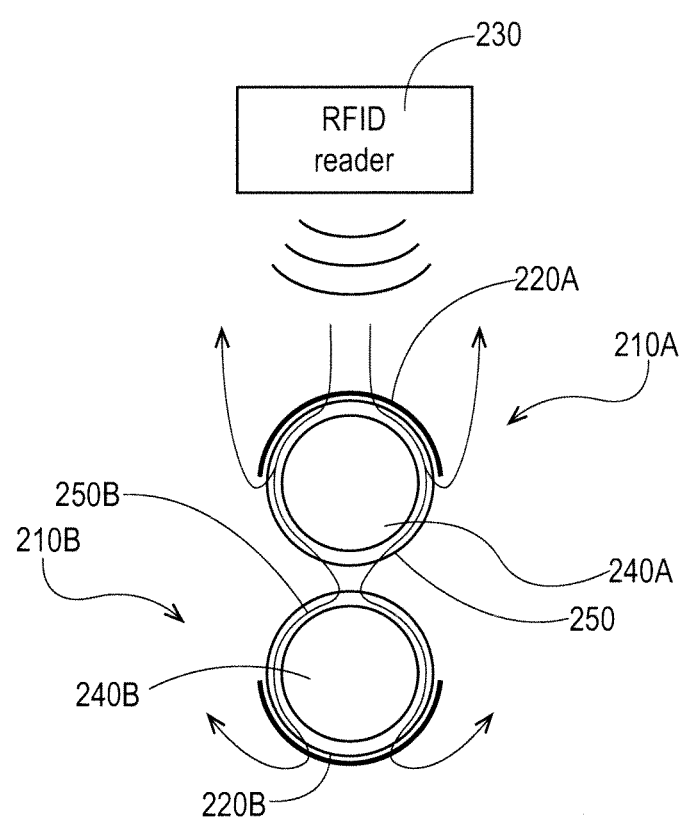

As shown in FIG. 2D, it is believed that even when the second article 210B is oriented such that the second communication device 220B is positioned away from the first article 210A, that sufficient signal coupling may be achieved between the second communication device 220B and the reader 230. Similarly, embodiments are contemplated where the first communication device 220A is positioned adjacent the reader 230, and embodiments are contemplated where the first communication device 220A is positioned away from the reader 230.

Due to the magnetic diverter 250, 250A, 250B, the magnetic flux and the induced voltage in the communication device 220, 220A, 220B could be sufficient for normal operation of the communication device 220, 220A, 220B even if the antenna is positioned away from the reader 230 and on the opposite side of the article 210, 210A, 210B.

As shown in FIGS. 2A-2D, the diverter 250, 250A, 250B, may cover a substantial portion of an outer surface of the article. In some embodiments, the diverter 250, 250A, 250B, may cover more than about 50 percent of the outer surface, more than about 60 percent, more than about 70 percent, more than about 80 percent, more than about 90 percent, less than about 100 percent, less than about 90 percent, less than about 80 percent, less than about 70 percent, less than about 60 percent, less than about 50 percent, or any number or any range within or including these values.

As stated previously, the overall dimensions of an article or product may be critical. As suggested herein, in some embodiments, the diverter can have minimal thickness. However, including the communication device, e.g. RFID tag, may prove difficult for such applications. The inventors have discovered that the RFID tag may be recessed in the diverter. In some embodiments, the diverter may comprise a recess. The communication device, e.g. RFID tag, may be disposed in the recess. The antenna of the communication device may be disposed on an outer surface of the diverter.

Embodiments are contemplated where a diverter is provided to a consumer separately from the article. For example, a consumer could obtain a diverter and fix the diverter to the article for which data was desired. The diverter may include a communication device already pre-attached or the consumer may also obtain the communication device separately from the diverter and attach thereto. In some embodiments, the diverter may be removable from the article and re-usable on subsequent articles. For such embodiments, the information provided by the communication device to a reader may be limited. For example, if the article were a disposable or a rechargeable battery, then the communication device and/or battery would have to be retrofitted such that the communication device could provide information regarding the remaining power level of the battery.

Increase of Signal Coupling

As stated above, one of the problems associated with creating a communication device for various products is realized when the communication device is utilized on conductive bodies. Additionally, antenna performance is severely degraded when antennas are placed near metals. In general, an RFID tag next to metallic body decreases signal coupling between the reader and the tag by 10×.

The inventors have discovered that by placing similarly tuned RFID tags and/or passive tuned loops near the RFID tag which is desired to be read, an increase in the readout range of the desired RFID tag occurs. This solution can be implemented in a wide variety of products where signal communication with a reader is desired.

Figure 3A:
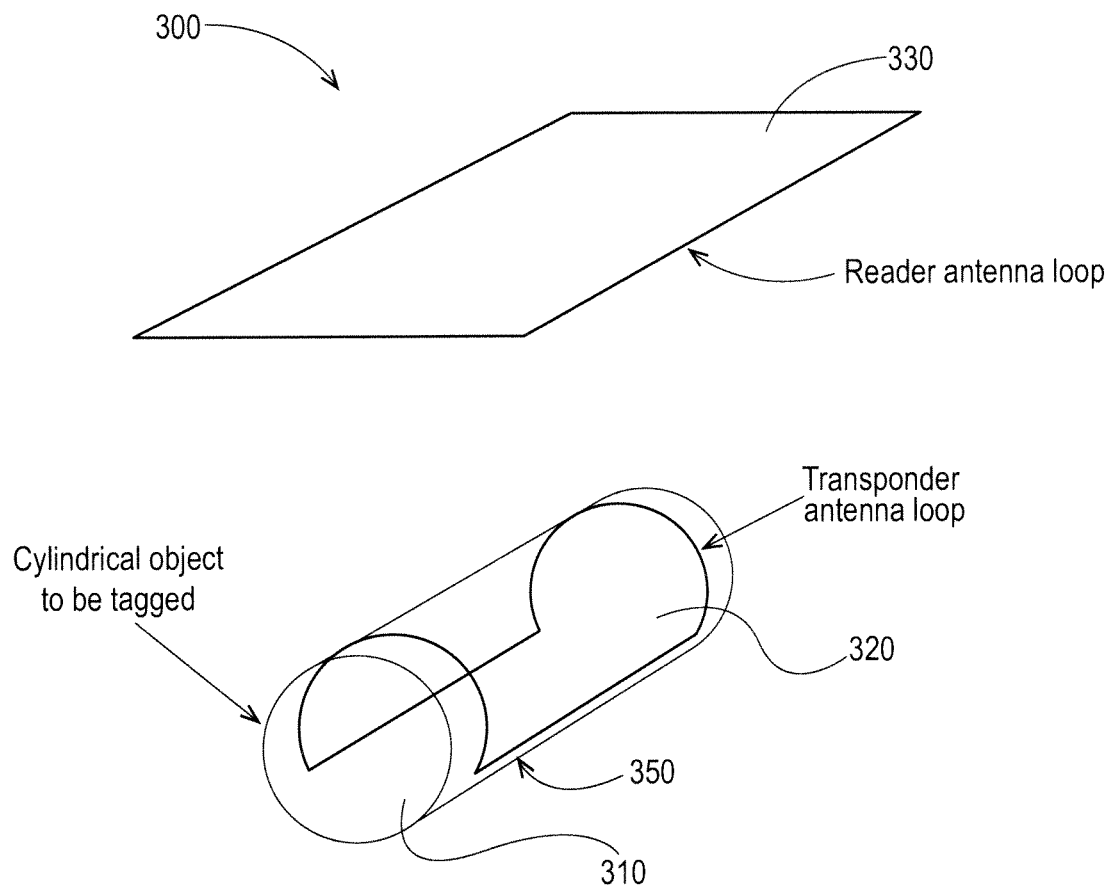
FIG. 3A is a schematic view showing an arrangement between a reader and an object having a communication device.
Figure 3B:
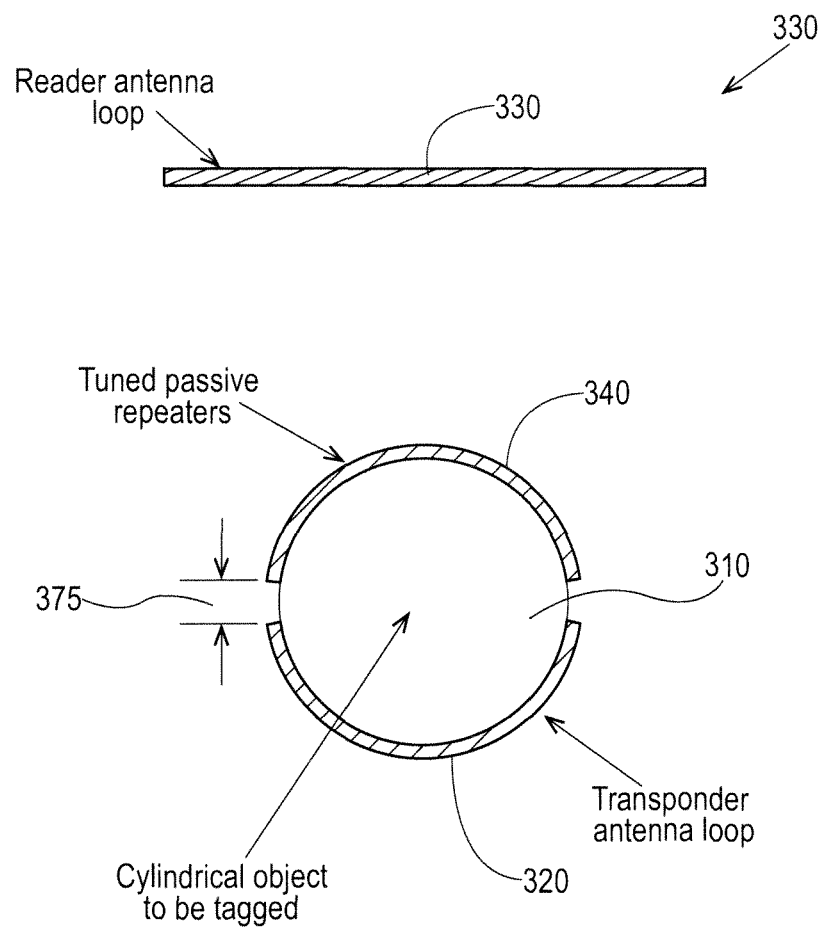
FIG. 3B is a schematic view showing the object of FIG. 3A including a passive repeater.

As shown in FIGS. 3A and 3B, a system 300 may comprise an object 310, e.g. battery, a communication device 320 and a reader 330. In operation, the reader 330, e.g. RFID reader or NFC (near field communications)-enabled smart phone, NFC enabled hand held device, could read data from the communication device 320. The communication device 320, e.g. RFID tag or other resonant RF circuit, smart sensor, etc., could be positioned on an outer surface 350 of the object 310 or therein. In order to increase the distance that the communication device 320 can broadcast, the system 300, may comprise a tuned repeater 340. The repeater 340 may be positioned on the object 310, or may be positioned adjacent to the object 310.

In some embodiments, the communication device 320 may comprise an RFID tag. In such embodiments, the RFID tag may have a resonant frequency and antenna. For such embodiments, where a repeater 340 is included, the repeater 340 may be tuned similar to the RFID tag. For example, the repeater 340 may have a second resonance frequency which is similar to that of the first resonance frequency.

The tuned repeater 340 can promote an increased amount of energy coupled into the reader 330 by the communication device 320 even when the communication device 320 is facing opposite the reader 330. In general, the amount of energy coupled into a reader decreases with increased distance from the communication device 320. However, with the inclusion of a repeater tuned to the same frequency as the communication device 320, e.g. RFID tag, and the reader 330, the amount of energy coupled between the communication device 320 and the reader 330 increases. The increase of signal coupling between the communication device 320 and the reader 330 with the utilization of the passive repeater 340 is discussed hereafter with regard to FIGS. 4 and 5.

Figure 3C:
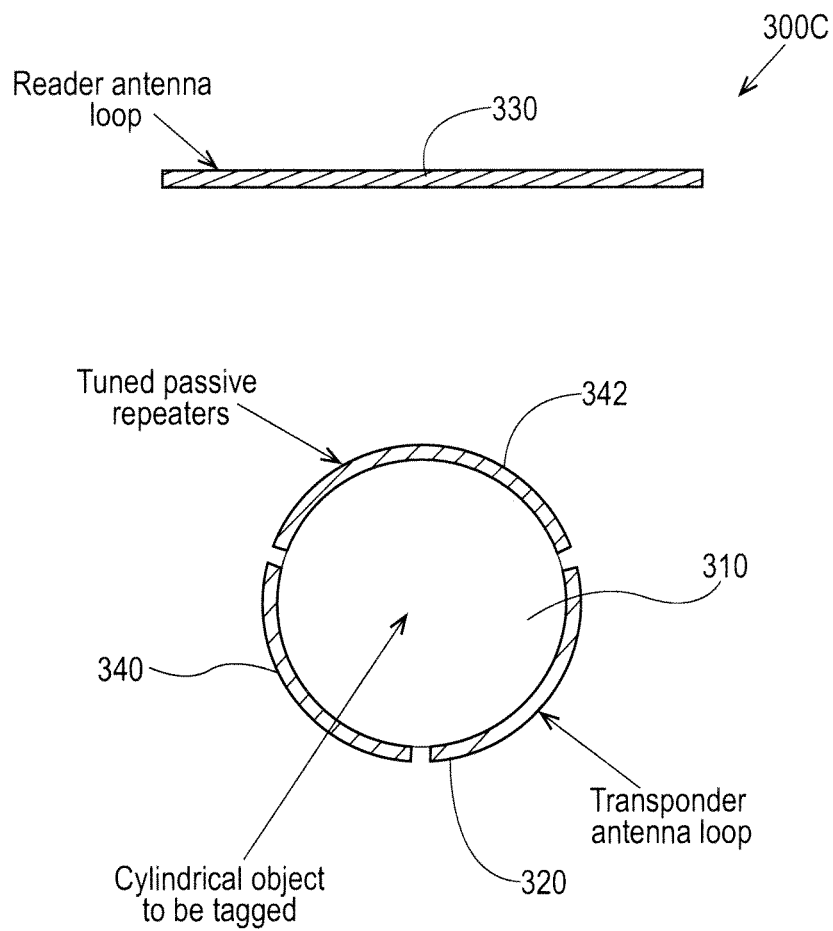
FIG. 3C is a schematic view showing the object of FIG. 3A including a plurality of passive repeaters.

Referring now to FIG. 3C, in some embodiments, a system 300C may comprise the object 310, e.g. battery, the communication device 320 and the reader 330. In operation, the reader 330 could read data from the communication device 320. The communication device 320 may be positioned on an outer surface 350 of the object 310 or therein. In contrast with the system 300, the system 300C, in order to increase the distance that the communication device 320 can broadcast, the system 300C, may comprise a plurality of repeaters 340, 342. The repeaters 340, 342 may be positioned on the object 310, or may be positioned adjacent to the object 310. While only two repeaters 340 and 342 are shown, embodiments are contemplated where more than two repeaters may be utilized.

Figure 3D:
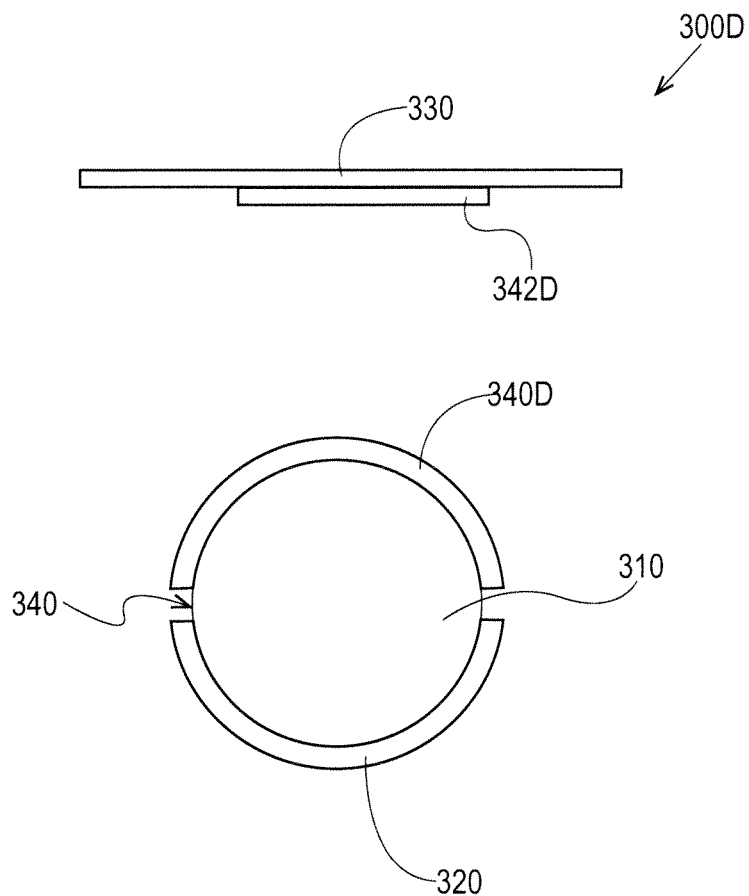
FIG. 3D is a schematic view showing an embodiment where the object of FIG. 3A includes a passive repeater and the reader of FIG. 3A included a passive repeater.

For those embodiments utilizing multiple repeaters, e.g. system 300D shown in FIG. 3D, at least one of the repeaters, e.g. 342D, may be positioned adjacent to the object. The system 300D may comprise the object 310, e.g. battery, the communication device 320 and the reader 330. In operation, the reader 330 could read data from the communication device 320. The communication device 320 could be positioned on an outer surface 350 of the object 310 or therein. The system 300D may further comprise a first repeater 340D and a second repeater 342D. The first repeater 340D may be positioned on the outer surface 350 of the object 310 similar to the communication device 320. The second repeater 342D may be positioned adjacent to the object 310. For example, as shown, the second repeater 342D may be positioned on the reader 330, e.g. between the first repeater 340D and the reader 330. Alternatively, it is believed that the second repeater 342D may be placed adjacent to the reader 330 to provide a similar effect of increasing signal coupling between the communication device 320 and the reader 330.

Figure 3E:
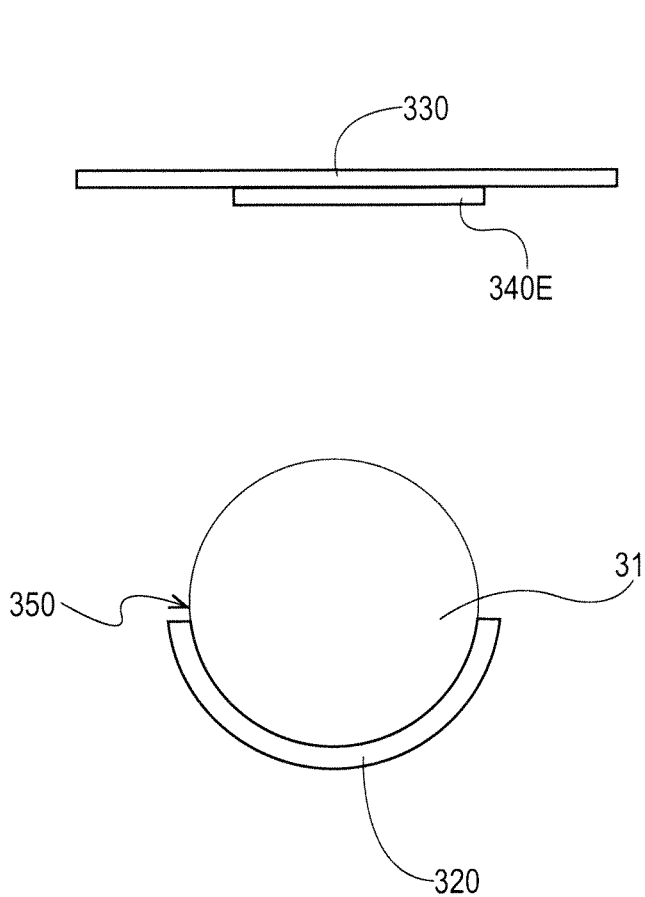
FIG. 3E is a schematic view showing another embodiment where the reader of FIG. 3A includes a passive repeater.

Referring to FIG. 3E, embodiments are contemplated where a system 300E comprises the object 310, e.g. battery, the communication device 320 and the reader 330. In operation, the reader 330 could read data from the communication device 320. The communication device 320 could be positioned on an outer surface 350 of the object 310 or therein. The system 300E may further comprise a repeater 340E. The repeater 340E may be positioned adjacent the object 310, e.g. between the communication device 320 and the reader 330. Alternatively, it is believed that the repeater 340D may be placed adjacent to the reader 330 to provide a similar effect of increasing signal coupling between the communication device 320 and the reader 330.

Additional embodiments are contemplated where a plurality of repeaters are provided on the object as well as adjacent thereto, e.g. on the reader. Other embodiments are contemplated where the reader comprises a plurality of repeaters while the object comprises the communication device 320.

Referring back to FIG. 3B, for those embodiments utilizing a single repeater or a plurality of repeaters which are positioned on the outer surface 350 of the object 310, the repeater(s) may be spaced from the communication device 320 and/or the antenna thereof such that the repeater does not physically contact the communication device 320 and/or antenna. A gap 375 may be between the repeater(s) and the communication device 320. In some embodiments, the gap 375 may be greater than about 1 mm, greater than about 5 mm, greater than about 10 mm, greater than about 20 mm, greater than about 30 mm, greater than about 40 mm, greater than about 50 mm, greater than about 60 mm, greater than about 70 mm, less than about 75 mm, less than about 70 mm, less than about 60 mm, less than about 50 mm, less than about 40 mm, less than about 30 mm, less than about 20 mm, less than about 10 mm, or any value and/or any range including or within the values provided.

As shown in FIGS. 3A-3E, the repeaters 340, 340D, 342 and/or the communication device 320 may conform to the outer surface 350 of the object 310. The repeaters may cover a substantial portion of the outer surface 350 of the object 310 and/or a substantial portion of the periphery of the object. The repeaters collectively may cover at least about 20 percent, at least about 30 percent, at least about 40 percent, at least about 50 percent, at least about 60 percent, at least about 70 percent, at least about 80 percent, at least about 90 percent and/or less than about 90 percent, less than about 80 percent, less than about 70 percent, less than about 60 percent, less than about 50 percent, less than about 40 percent, or any number or any range including or within the above values. Similarly, the communication device 320 may cover a substantial portion of the outer surface 350 of the cylindrical object 310 and/or a substantial portion of the periphery of the object as described above with regard to the repeaters.

It is believed that by conforming the communication device 320 and/or the repeaters to the outer surface 350 of the object, the signal communication between the communication device 320 and the reader 330 can be provided at a variety of angles. For example, where the communication device has its face oriented in a direction away from the reader, the inclusion of repeaters or by conforming the communication device to the periphery of the object, signal communication between the reader and the communication device may still be able to be established.

Regarding the periphery of the object, the coverage described above is in the context of the periphery of the cross section taken generally perpendicular to a long dimension of the object.

As mentioned previously, the inclusion of the repeater is believed to increase the signal coupling between the communication device 320 and the reader 330. FIG. 4 graphically illustrates the differences in signal coupling between systems utilizing no repeater and those systems utilizing a passive repeater between the communication device and the reader.

As shown in FIG. 4, curve 470 shows the computer simulated model of the signal coupling between a communication device and a reader that are positioned 64 mm apart from one another. At the peak of curve 470, the signal coupling is approximately 2.0 percent. Curve 480 represents the signal coupling for those embodiments that utilize at least one repeater positioned between the communication device and the reader. In contrast to the curve 470, at the peak of curve 480 the signal coupling is about 3.7 percent. As such, it is believed that the inclusion of the repeater between the communication device and reader can increase the signal coupling by about 85 percent. The presence of the passive repeater can change the resonant frequency of nearby resonators and require fine system-level tuning to keep all circuits in resonance. As such, the peak of the curve 480 may be offset from the peak of curve 470.

Any suitable percentage increase in signal coupling may be realized. For example, in some embodiments, the increase in signal coupling may be greater than about 1 percent, greater than about 5 percent, 10 percent, greater than about 20 percent, greater than about 30 percent, greater than about 40 percent, greater than about 50 percent, greater than about 60 percent, greater than about 70 percent, greater than about 80 percent, greater than about 85 percent, greater than about 90 percent, greater than about 100 percent, less than about 90 percent, less than about 85 percent, less than about 80 percent, less than about 70 percent, less than about 60 percent, less than about 50 percent, less than about 40 percent, less than about 30 percent, less than about 20 percent, or any number or any range including or within the values provided above.

Figure 5:
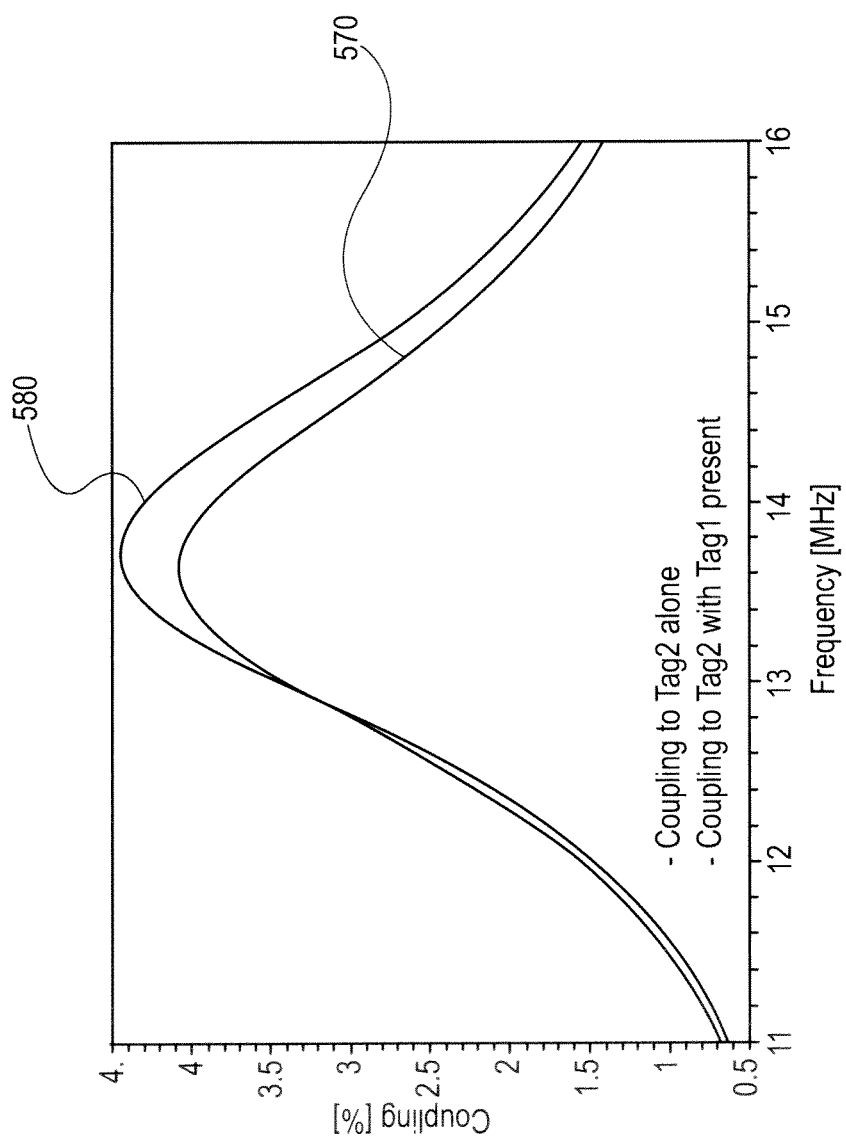
FIG. 5 is a graphical representation showing a computer simulated model of the signal coupling between a first object and a first reader versus a second object and a second reader including a passive repeater adjacent the second reader.

FIG. 5 graphically illustrates the differences in the computer simulated model of the signal coupling between systems utilizing no repeater and those systems utilizing a passive repeater adjacent the reader.

As shown in FIG. 5, curve 570 shows the signal coupling between a communication device and a reader that are positioned apart from one another. At the peak of curve 570, the signal coupling is approximately 4.00 percent. Curve 580 represents the signal coupling for those embodiments that utilize at least one repeater positioned adjacent the reader. In contrast to the curve 570, at the peak of curve 580 the signal coupling is about 4.40 percent. As such, the inclusion of the repeater between the communication device and reader is believed to increase the signal coupling by about 10 percent. In some embodiments, this configuration may yield lower signal coupling increases or higher, e.g. greater than 1 percent, greater than 2 percent, greater than 3 percent, greater than 5 percent, greater than about 7 percent, greater 10 percent, greater than about 12 percent, greater than 15 percent, less than about 12 percent, less than about 10 percent, less than about 9 percent, less than about 8 percent, less than about 7 percent, less than about 5 percent, less than about 3 percent, less than about 2 percent or any number or any range including or within these values. Similar to the curves shown in FIG. 4, the inclusion of the passive repeater can shift the peak of curve 580 with respect to the peak of curve 570.

Figure 6:
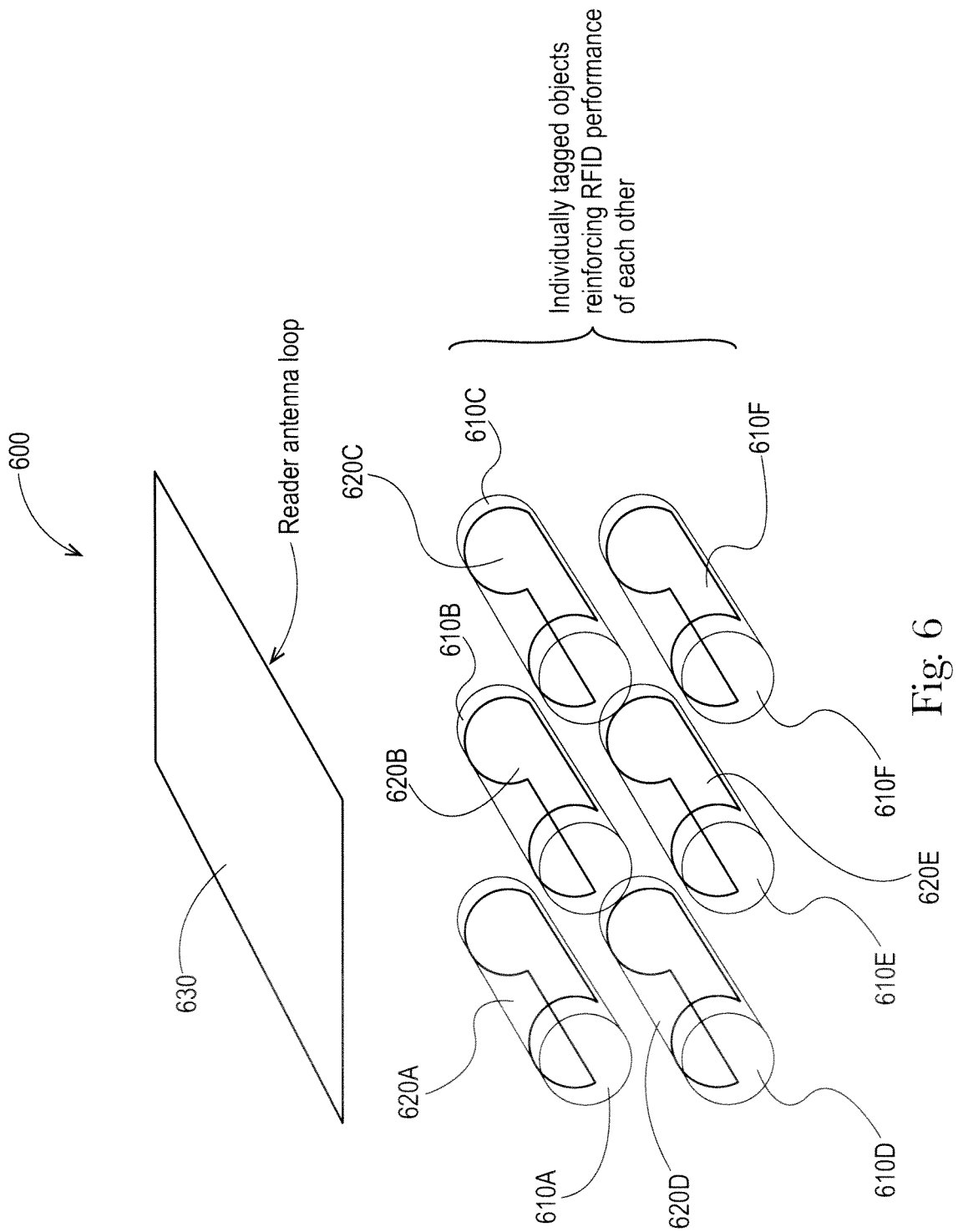
FIG. 6 is a schematic view showing an embodiment where a plurality of objects is arranged with respect to a reader.

Referring to FIG. 6, it has been discovered that the use of multiple communication devices, e.g. RFID tags, adjacent one another can similarly increase the signal coupling between a desired communication device and a reader. For example, a system 600 may comprise a plurality of objects, e.g. 610A, 610B, 610C, 610D, 610E, and 610F, and a reader 630. In some embodiments, each of the objects, e.g. 610A, 610B, 610C, 610D, 610E, and 610F, may comprise a communication device, e.g. 620A, 620B, 620C, 620D, 620E, and 620F, respectively. Each of the communication devices may be positioned on an outer surface of its respective object. In operation the reader 630 would transmit signals to and from at least one of the communication devices, e.g. 620A, 620B, 620C, 620D, 620E, and 620F.

Each of the communication devices, e.g. 620A, 620B, 620C, 620D, 620E, and 620F, may have resonance frequencies which are similar to one another.

Because an increase in signal coupling can be achieved with the utilization of communication devices, communication devices may be utilized in the previous embodiments including repeaters. Due to cost reasons, replacing every repeater with a communication device may be expensive to achieve. However, embodiments, are contemplated where a system comprises a plurality of communication devices and at least one repeater. The plurality of communication devices may individually be conformed on the outer surface of a respective object where the objects are positioned adjacent one another. Additionally, at least one communication device may be positioned between at least one of the objects of the plurality of objects and the reader.

Embodiments are contemplated where the objects are disposable or rechargeable batteries. For such embodiments and all the embodiments described herein, the proposed communication device may comprise an electronic sensor capable of measuring battery voltage, an analogue-to-digital converter which can covert the measured battery voltage into a binary number, a memory device, front end circuitry, and an antenna.

The analogue-to-digital converter should have sufficient bit length to convert the measured battery voltage into a binary number with the same bit length to achieve sufficient resolution in the voltage measurement. The memory device may be utilized to store the converted analogue measurement value as well as the tag identification number and any other relevant data, e.g. history of the object, history of use of the object, etc.

The front end circuitry may be utilized to convert the incoming signal from the reader into DC current to power the communication device. For such embodiments, the communication device may be passive. Specifically, where the communication device derives power indirectly from RF signals from a reader or from another source, the communication device is passive. In contrast, where the communication device is in electrical communication with a power source, the power source not being the data signal, the communication device is active. The communication device for utilization in any of the embodiments described herein may be passive or active or hybrid (battery assisted to continuously "listen" without being powered by the reader for improved range of operation). In the case of disposable or rechargeable batteries, passive communication devices are attractive as they do not require power from the disposable or rechargeable battery. The front end circuitry can further transmit the contents of the memory back to the reader in a pre-defined protocol.

The antenna may be tuned to the incoming radio frequency to efficiently transfer the incoming signal, e.g. radio frequency, into the front end circuitry and to re-radiate the same signal modulated with the contents of the digital data back to the reader.

For those embodiments where the objects are disposable or rechargeable batteries, determining remaining power levels of the batteries is facilitated for the consumer. For example, with the utilization of repeaters and/or communication devices as described heretofore, the signal coupling between the reader and the object is increased.

As an example in the increase in signal coupling, in some embodiments, the system may comprise an electronic device. The electronic device may comprise a recess in which at least one object, e.g. a disposable or rechargeable battery, is positioned. By utilizing the repeater or communication device as described heretofore, a consumer may be able to obtain information regarding the remaining energy in the disposable or rechargeable battery while the disposable or rechargeable battery is still within the electronic device. As an example, batteries in a remote control toy may utilize the invention(s) described herein. The batteries may be positioned in a recess and equipped with communication devices. A door for sealing the recess and the batteries may comprise a separate communication device and/or a repeater. This can allow the user to determine the remaining service life of the battery while still positioned within the electronic device.

Additional information may be provided to the consumer. For example, data on the history of the battery, e.g. the last measured voltage of the battery, date and time of the measured voltage. This may be beneficial in providing a projected remaining lifetime of the rechargeable or disposable batteries.

The electronic device may comprise a cover which engages with a portion of the electronic device to at least partially cover the object, e.g. disposable/rechargeable battery. In accordance with the embodiments described heretofore, the cover may comprise a repeater or a communication device in order to increase the signal coupling between the disposable or rechargeable battery and the receiver. For those embodiments, where the cover comprises a communication device, the communication device may provide additional information to the consumer regarding the electronic device. The reader may be programmed to calculate and display remaining runtime based on the device load information. Embodiments are contemplated where the repeater or the communication device comprised by the cover is a sticker which is later attached to the cover by the consumer. Similarly, embodiments are contemplated where the repeater or the communication device is a sticker and is applied to the receiver.

As described previously, the repeaters may comprise passive loops tuned similarly to the communication devices. In some embodiments, the repeaters may comprise multiple communication devices, e.g. RFID tags.

Rotational Diversity

An additional issue which may occur is due to rotational orientation of the object/article. Generally, the configuration of the communication device is intended for readout with the receiver in such a position which is parallel with the antenna. Readout from the ends of the object may not be possible. Similarly, readout may not be possible when the reader is parallel to the object but perpendicular to the tag antenna.

Figure 7A:
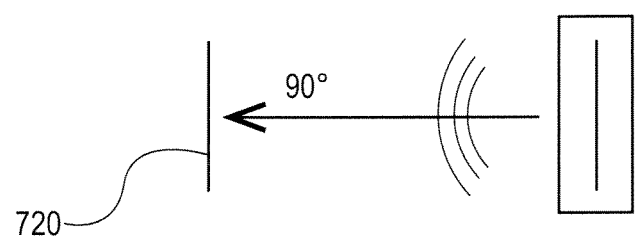
FIGS. 7A and 7B are schematic views different angles of orientation between an object and a reader.
Figure 7B:
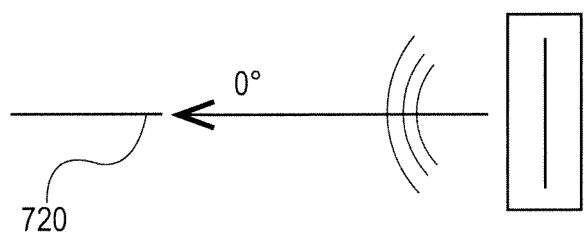

Typically there is an imbalance in the signal magnitude between the two sides of the object. As shown in FIG. 7A, a peak of the radiation pattern is when a reader 730 is facing the communication device 720. In contrast, as shown in FIG. 7B, the radiation pattern reduces to zero in when the reader 730 is rotated perpendicular to the communication device 720. Additionally, the readout range when the communication device 720 is exactly on the opposite side is significantly lower compared to the case when the antennas are facing each other.

Figure 8:
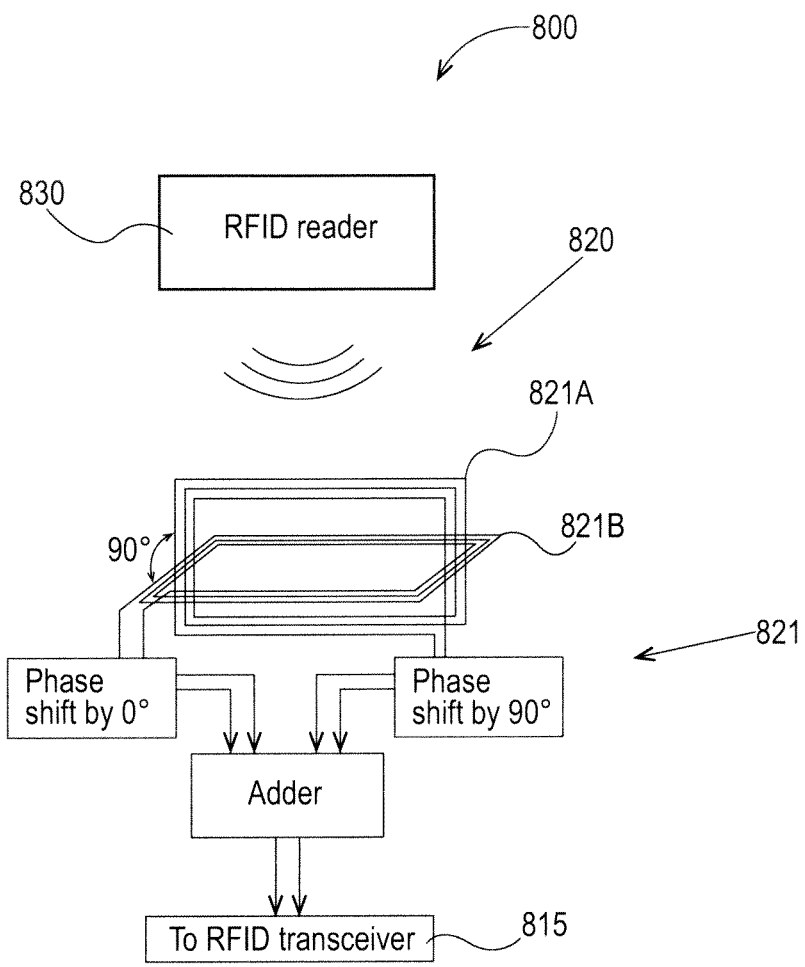
FIG. 8 is a schematic view showing an embodiment where an object comprises multiple antennas.

As shown in FIG. 8, a system 800 may comprise a receiver 830, and a communication device 820. The communication device 820 may comprise a first antenna 821A and a second antenna 821B. The signal from the second antenna 821B may go through a phase shifting circuit (RC circuit) to shift the voltage of the second loop by 90 degrees to bring the voltages in phase to the input of an analogue adder circuit. The resulting voltage is applied to the input of an RFID transceiver 815. In such embodiments, the signal from the first antenna 821A may not go through the phase shifting circuit.

The antenna 821 may be provided with additional portions for enhancing signal coupling at additional angles. For those embodiments including additional portions, a phase shifting network may also be included for combining the signals from all antennae in phase. The phase shifting could be done by any suitable means. For example, the phase shifting could be done by a passive RLC network.

The induced signal in the 2-antenna configuration as a function of the angle $\theta$ between the plane of the reader antenna and the plane of one of the communication device antennae 821 is $V=A_0(\sin\theta+\cos\theta)$, and never drops to zero. A resulting radiation pattern calculated in comparison to the calculated radiation pattern of a single antenna and the unit circle is given in FIG. 9.

Figure 9:
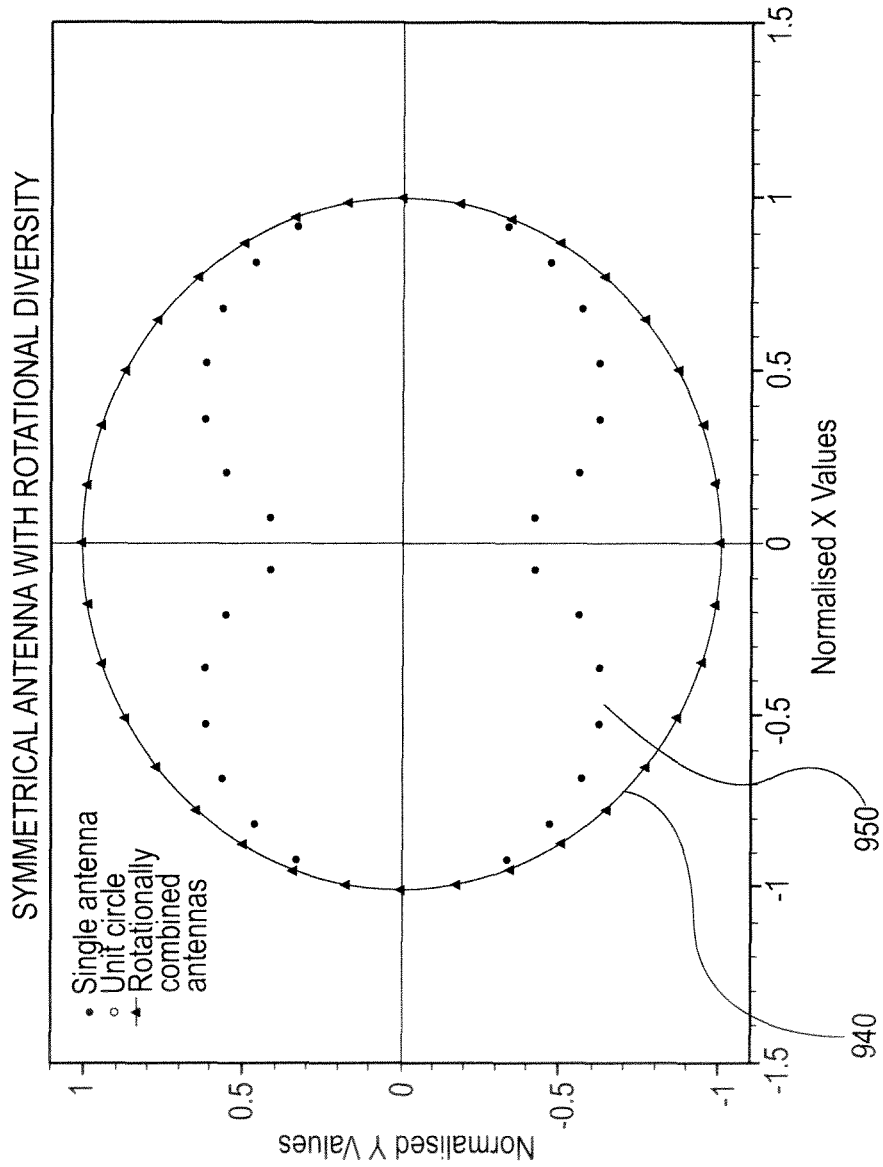
FIG. 9 is a graphical representation showing a computer simulated model of a resulting radiation pattern from the multiple antennas of FIG. 8.

As shown in FIG. 9, an arcuate line 940 shows the computer simulated model of a radiation pattern utilizing the first antenna 821A and the second antenna 821B as described above. The arcuate line 950 shows the calculated radiation pattern for a single antenna.

Embodiments are contemplated where the reader comprises an antenna constructed similar to the antenna 821. Namely, the antenna of the reader may comprise a first portion and a second portion which are offset from each other by a particular angle, e.g. 90 degrees. Also, embodiments are contemplated where the object comprises the antenna 821 as described heretofore and the reader comprises an antenna configured similar to the antenna 821. For those embodiments where the reader comprises an antenna configured similar to the antenna 821, additional portions may be utilized in the antenna 821 and/or the antenna of the reader.

The embodiments described with regard to FIGS. 8 and 9 can provide increased signal coupling between the reader and the object at angles of orientation of the reader which were heretofore problematic.

Measurements based upon a prototype using multiple antennas as described in FIGS. 8 and 9 are provided with regard to FIGS. 13A and 13B and 14A and 14B. Regarding 13A and 13B, measurements of the incident field were taken with respect to the field having the direction 1380 about an object 1310. A plot 1360 shows the measured values at various angles with regard to the object 1310. In contrast plot 1340 shows the calculated values. As shown for both plots 1340 and 1360, in the area between 180 degrees and 270 degrees, the measured values differ from the calculated values by a larger margin than anywhere else on FIG. 13A. However, the radiation pattern is fairly uniform about the object 1310 in the direction 1380. So, the embodiments described with regard to FIGS. 8 and 9 can produce rotational diversity about the object 1310 in the direction 1380.

Figures 14A, 14B:
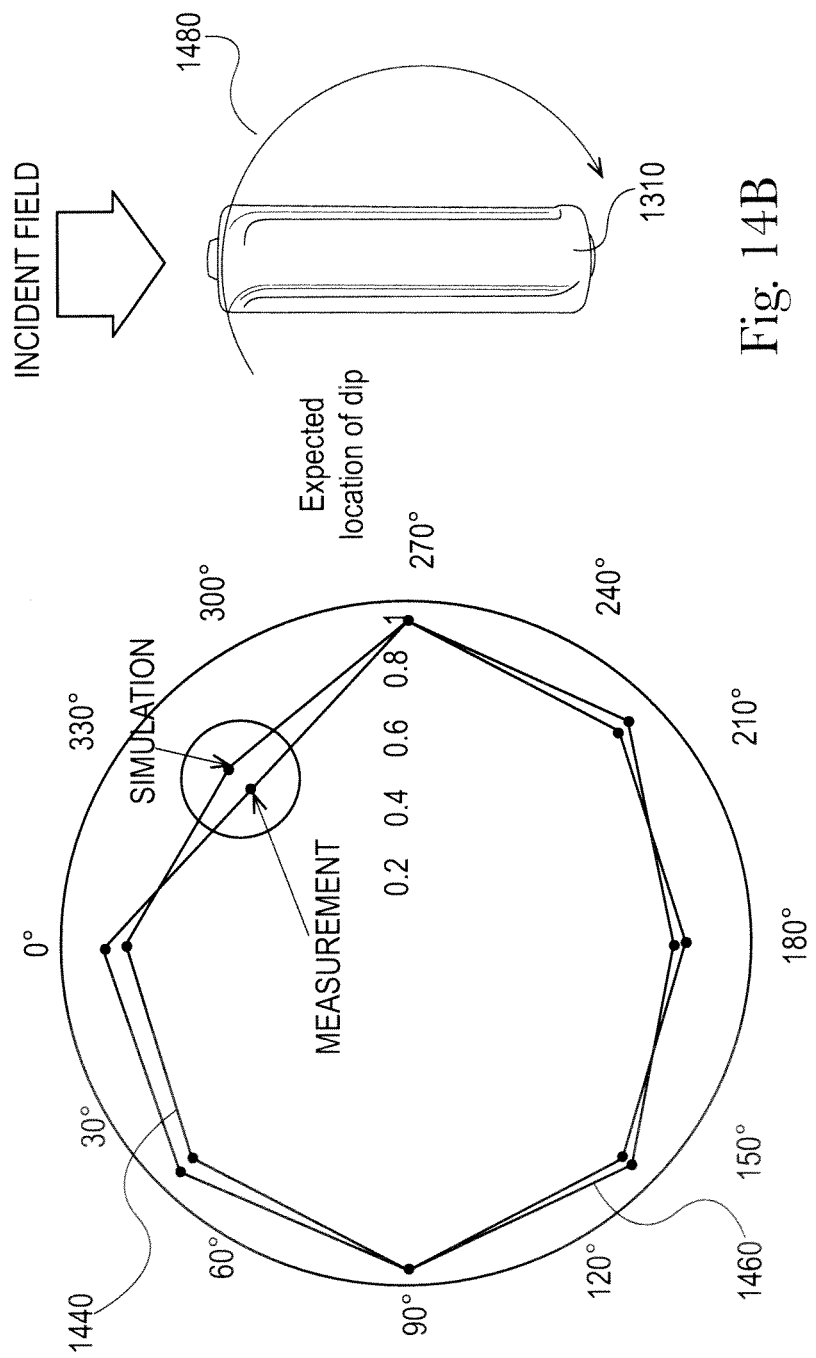
FIG. 14A is a graphical representation showing measured values of an incident field for the antennas of FIG. 8.
FIG. 14B is a schematic view showing a direction for the incident field of FIG. 14A.

Regarding, FIGS. 14A and 14B, measurements of the incident field were taken with respect to the field having the direction 1480 about an object 1310. A plot 1460 shows the measured values at various angles with regard to the object 1310. In contrast plot 1440 shows the calculated values. As shown for both plots 1440 and 1460, in the area between 270 degrees and 0 degrees, the measured values differ from the calculated values by a larger margin than anywhere else on FIG. 14A. However, similar to the plot shown in FIG. 13A, the radiation pattern is fairly uniform about the object 1310 in the direction 1480. So, the embodiments described with regard to FIGS. 8 and 9 can produce rotational diversity about the object 1310 in the direction 1480.

Rotational Orientation of the Object:

Additional measures can be taken to ensure that the range of null angles is reduced. In general, the readout range between any two loop antennas is not uniform for all angular positions of the two antennas with respect to each other. There are some angles when the readout is impossible due to the lack of magnetic coupling. Such angles are termed "nulls".

As described previously, a rectangular loop antenna may be bent to conform to the outer periphery of the object; however, in this configuration the conformed rectangular antenna inherently prefers one side of the object to the other when a reader is positioned in parallel to the cylinder and rotated around the cylinder axis (equivalent to the reader being fixed and the cylinder being rotated around its own axis). As such, when the rectangular antenna is facing the receiver, signal coupling is good. However, when the rectangular antenna is facing away from the receiver, the signal coupling between the rectangular antenna and the receiver is decreased. As such, the rotation of the object may cause nulls to occur.

As discussed previously, the utilization of repeaters may alleviate this problem. The repeaters are discussed in detail with regard to FIGS. 3A-6.

Additionally, in an effort to increase the symmetry of the signal magnitude between the two sides, the inventors have devised a unique configuration for a communication device. The configuration may comprise the communication device or may comprise only portions of the communication device.

For example, in some embodiments, the unique configuration could comprise the antenna of the communication device. For the sake of clarity reference will be made to the communication device and will encompass configurations of the entire communication device or portions thereof, e.g. antenna.

Figure 10B:
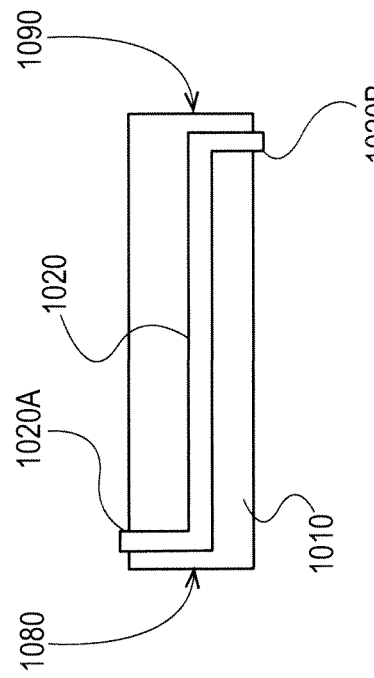
FIGS. 10A and 10B are schematic views showing another embodiment of a communication device and/or antenna of the present invention.
Figure 10A:
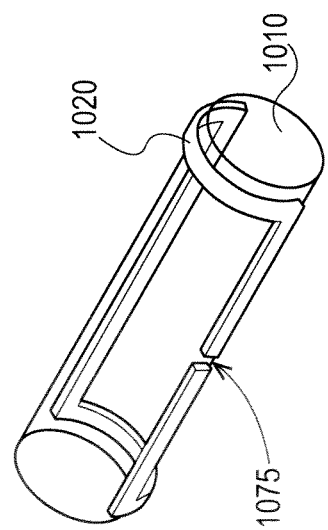

The proposed communication device can increase the symmetry of the signal magnitude between the two sides of the object and 360 degrees around it. As shown in FIGS. 10A and 10B, where an object 1010 has a cylindrical shape, a communication device 1020 may be provided. The communication device 1020 may comprise a first portion 1020A disposed adjacent to a first end 1080 of the object 1010 and a second portion 1020B disposed adjacent to a second end 1090. The first portion 1020A and the second portion 1020B may be longitudinally offset. The first portion 1020A may extend about the circumference (outer periphery) of the object 1010 for about 180 degrees. In contrast, the second portion 1020B may extend about the circumference (outer periphery) of the object 1010 for about 180 degrees. The 180 degrees covered by the first portion 1020A may correspond to zero degrees to 180 degrees while the 180 degrees covered by the second portion 1020B may correspond to 180 degrees to 360 degrees. As such the 180 degree sweep of the object 1010 by the first portion 1020A may be opposite the 180 degree sweep of the object 1010 by the second portion 1020B.

The configuration of the communication device 1020 of FIGS. 10A and 10B can shift the null angle which helps reading from the side at 90 deg, e.g. when the reader is perpendicular to the antenna. The nulls may be shifted to about 45-60 deg. which is an inconvenient angle, and the consumers are not expected use it.

Figure 11:
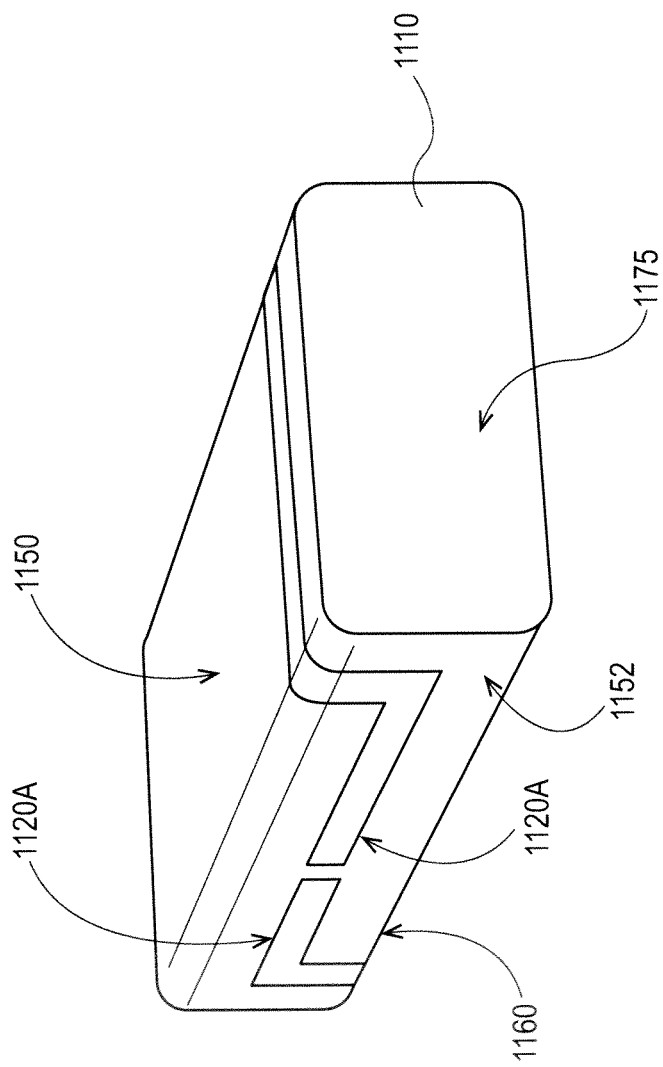
FIG. 11 is a schematic view showing another embodiment of a communication device and/or antenna of the present invention.

Although FIGS. 10A and 10B show the object 1010 as a cylinder, the communication device 1020 described above may be applied to any object of any size and/or shape. For example, a 9 volt battery is typically non-cylindrical and instead has more of a rectangular cross section. The communication device similar to the communication device 1020 described above may be applied to the 9 volt battery in a similar manner. As shown in FIG. 11, an object 1110 may be non-cylindrical and still utilize a communication device 1120. Again, for the sake of clarity, the communication device 1120 may be configured similar to the communication device 1020 or the antenna of the communication device 1120 may be configured as described heretofore regarding the antenna of the communication device 1020.

The antenna 1120 may comprise a first portion 1120A and a second portion 1120B. The first portion 1120A may be disposed on a first face 1150 and a portion of sides faces 1152. The second portion 1120B may be disposed on a second face 1160 and a portion of the side faces 1152.

For those objects which are non-cylindrical, the outer circumference of the object can be used approximate the degrees of sweep covered by an antenna or portion thereof. As an example, referring back to FIG. 11, a face 1175 of the object 1110 may be encircled and thereby used to approximate the angle of sweep covered by the antenna(s) or portions thereof.

It is believed that utilization of the antenna 1020 and 1120 described herein may provide a more balanced signal radiation pattern. Additionally, utilization of the antennas 1020 and 1120 may allow a reader to be adjacent an end of the object, e.g. 1010, 1110, and still read the data from the communication device.

The design of the antennas and/or communication devices described herein may influence greatly the areas where signal reception by the reader is difficult. While the maximum readout range depends on the transmitted power, in part, the position of the nulls are entirely dependent on the geometry and physical arrangement of the antennas, and is completely independent of other electrical parameters such as power, inductance, resonance frequency etc.

The curved sides of the tag antenna closing on the opposing sides of the cylinder can provide readout on the ends of the object as opposed to a conventional antenna. However, depending on the design of the antenna(s), the angular position of nulls can be changed by changing the so called "aspect ratio" of the antenna(s). The aspect ratio is defined by the ratio of the cylinder diameter D to the length of the antenna l, i.e. D/l. The diameter of the cylinder is a given parameter depending on the size of the object, but the ratio can be changed by varying the length of the antenna within the constraints of the object length. For a situation where D/l approaches zero, an infinitely long antenna, the tag antenna will approximate a planar loop antenna and the angular location of the nulls will approach the ends of the object. In contrast, l may be forced to approach zero, hence making D/l approach infinity. For such cases the antenna may approximate a loop antenna wrapped around the object. In such a case, the nulls will be rotated by 90 degrees to the cylinder side walls. It is possible to move the position of the nulls to any position in between these two limits by varying the length of the antenna, depending on where, in the present application, "natural" or "intuitive" readout angles are considered to be.

The principle of shifting nulls of the antenna radiation pattern to any desirable angular position through the adjustment of the antenna geometry would be applicable to any number of antenna and device types and not limited to cylindrical objects.

Embodiments are contemplated where the objects are configured with an antenna which is custom tailored for its end use. For example, where the reader is expected to read from the ends of the object, a first antenna configured to allow reading from the ends of the object may be provided. Where the reader is expected to read from the sides of the object, a second antenna configured to allow reading from the sides of the object may be provided. So, where the object is an AA battery, a first AA battery may comprise a first antenna allowing reading from the ends of the AA battery. Additionally, a second AA battery may comprise a second antenna allowing reading from the sides of the second AA battery.

A plurality of first AA batteries may be packaged together. A plurality of second AA batteries may be packaged together. Additionally, in some embodiments, a first AA battery and a second AA battery may be packaged together or a plurality either or both.

Figure 12A:
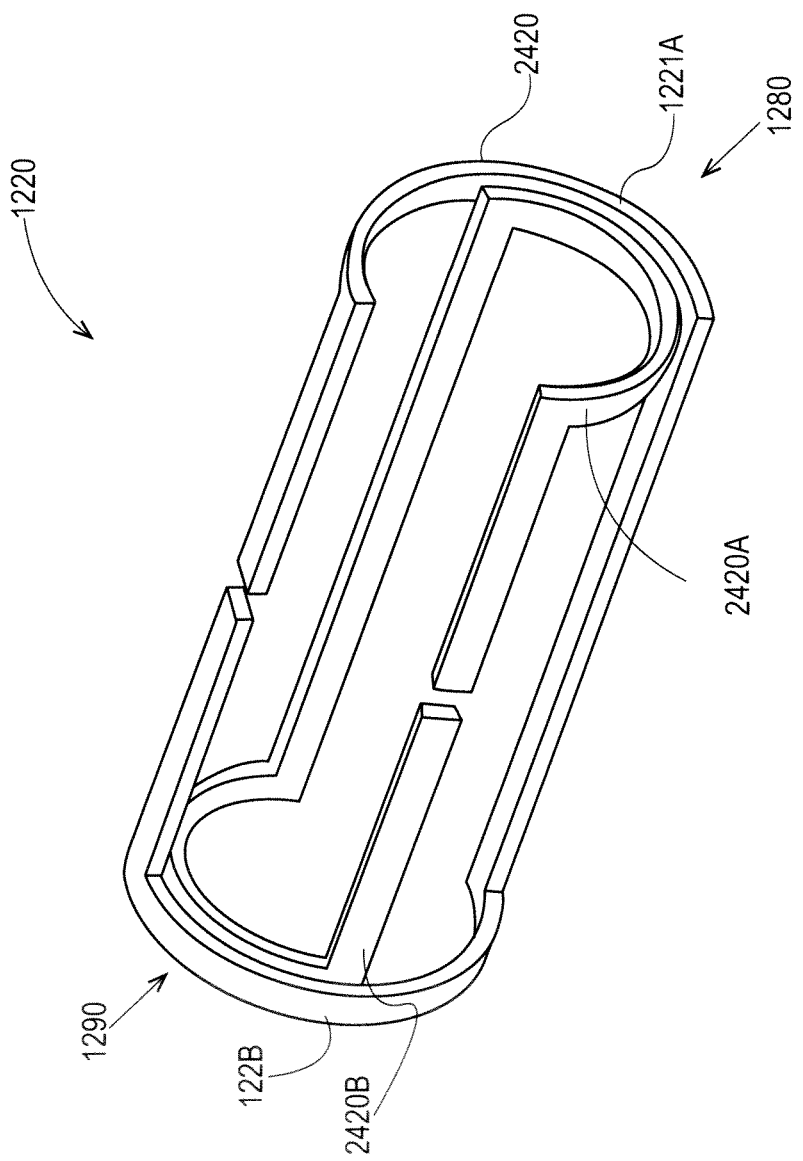
FIG. 12A is a schematic view showing another embodiment of a communication device and or antennas of the present invention.
Figure 13B:
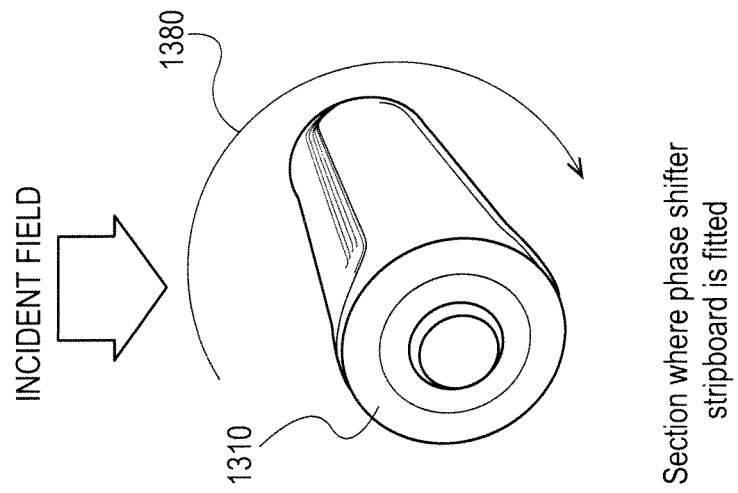
FIG. 13B is a schematic view showing a direction for the incident field of FIG. 13A.
Figure 13A:
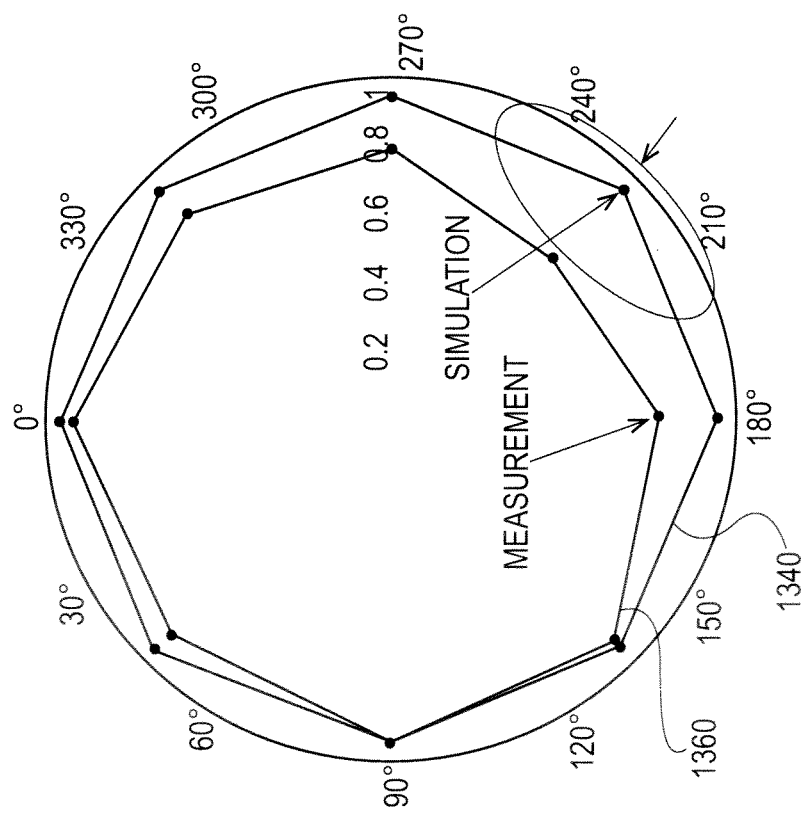
FIG. 13A is a graphical representation showing measured values of an incident field for the antennas of FIG. 8.

Embodiments are contemplated where an object comprises a communication device which incorporates several of the aspects described herein. As an example, an object may comprise a communication device having a configuration as shown in FIG. 12A. A communication device 1220 and/or antenna shown in FIG. 12A may be configured similar to the communication devices 1020 and 1120 shown in FIGS. 10 and 11. As such, the communication device 1220 may comprise an antenna 1221 having a first portion 1221A and a second portion 1221B. The first portion 1221A and the second portion 1221B may be oppositely positioned from one another—both on opposite ends of the object but also on opposite faces.

The communication device 1220 may further comprise a second antenna 2420 having a first portion 2420A and a second portion 2420B. The first portion 2420A and the second portion 2420B may be oppositely positioned from one another—both on opposite ends of the object but also on opposite faces.

FIGS. 12B and 12C show the overlap between the first antenna 1221 and the second antenna 2420. FIG. 12B shows the communication device 1220 when viewed from a first end 1280 looking toward a second end 1290. The first portion 1221A of the first antenna 1221 may cover about 180 degrees of a cylindrical object. The 180 degrees may be in a first quadrant I and a fourth quadrant IV. Similarly the first portion 2420A of the second antenna may cover about 180 degrees of a cylindrical object. The 180 degrees may be in a third quadrant III and the fourth quadrant IV. The first portion 1221A of the first antenna 1221 and the first portion 2420A of the second antenna 2420 may overlap with one another in the fourth quadrant IV, e.g. section 2021.

The second portion 1221B of the first antenna 1221 may cover about 180 degrees of a cylindrical object. The 180 degrees covered by the second portion 1221B of the first antenna may be opposite that of the first portion 1221A. For example, the 180 degrees covered by the second portion 1221B may be in a second quadrant II and the third quadrant III. Similarly, the second portion 2420B of the second antenna 2420 may cover about 180 degrees of a cylindrical object. The 180 degrees covered by the second portion 2420B may be opposite that of the first portion 2420A. For example, the 180 degrees covered by the second portion 2420B may be in the first quadrant I and the second quadrant II. The second portion 1221B of the first antenna 1221 and the second portion 2420B of the second antenna 2420 may overlap with one another in the second quadrant II, e.g. section 2022.

For most objects, the first antenna 1221 and the second antenna 2420 may be positioned such that the first antenna 1221 is positioned within the second antenna 2420 or vice versa. Where space constraints are an issue, the first antenna 1221 and the second antenna 2420 may be positioned sequentially such that the first portion 1221A of the first antenna 1221 is positioned directly behind the first portion 2420A of the second antenna 2420. In some embodiments, the antennas described in FIGS. 12A-12C may be printed on both sides of a flexible substrate. This can help minimize the overall dimensions added to the object.

For the embodiments described in FIGS. 12A-12C, the communication device 1220 may comprise a phase shifter to bring the voltages in phase between the first antenna 1221 and the second antenna 2420.

Several embodiments have been provided heretofore which can provide for increased signal coupling between a communication device and a reader. Embodiments are contemplated where an article comprises a communication device configured as described in FIGS. 8-9. In such embodiments, the article may be comprised by a system which includes a reader. Furthermore, in such embodiments, the article and/or the reader may comprise a repeater. Alternatively, the system may comprise a repeater positioned between the article and the reader. Additionally, where the article comprises a conductive body, the article may further comprise a diverter. In such embodiments, the communication device may be disposed on an outer surface of the diverter or adjacent thereto.

Embodiments are contemplated where an article comprises a communication device configured as described with regard to FIGS. 10A and 10B. In such embodiments, the article may be comprised by a system which includes a reader. Furthermore, in such embodiments, the article and/or the reader may comprise a repeater. Alternatively, the system may comprise a repeater positioned between the article and the reader. Additionally, where the article comprises a conductive body, the article may further comprise a diverter. In such embodiments, the communication device may be disposed on an outer surface of the diverter or adjacent thereto.

Embodiments are contemplated where an article comprises a communication device configured as described with regard to FIGS. 12A-12C. In such embodiments, the article may be comprised by a system which includes a reader. Furthermore, in such embodiments, the article and/or the reader may comprise a repeater. Alternatively, the system may comprise a repeater positioned between the article and the reader. Additionally, where the article comprises a conductive body, the article may further comprise a diverter. In such embodiments, the communication device may be disposed on an outer surface of the diverter or adjacent thereto.

Embodiments are contemplated where an article comprises a system having an article and a reader. The article may comprise a communication device configured as described in any of the embodiments herein. In such embodiments, the article and/or the reader may comprise a repeater. Alternatively, the system may comprise a repeater positioned between the article and the reader. Additionally, where the article comprises a conductive body, the article may further comprise a diverter. In such embodiments, the communication device may be disposed on an outer surface of the diverter or adjacent thereto.

Embodiments are contemplated where an article comprises a communication device configured as described in any of the embodiments herein. The article may be comprised by a system which includes a reader. Where the article comprises a conductive body, the article may further comprise a diverter. In such embodiments, the communication device may be disposed on an outer surface of the diverter or adjacent thereto.

Wireless Charging

A RFID link is in essence a wireless resonant energy transfer link, utilizing the transferred energy to power a tag containing a specific identification number. The tag may optionally include various sensors and able to communicate its identification and any sensor information back to the reader device through the use of the same media. All the inventions listed herein are applicable to wireless resonant energy transfer. Hence, the embodiments described herein allow for an omni-directional wireless charging system for battery charging as well as for RFID communications. Specifically, the embodiments described herein improve the efficiency of charging. For example, it is believed that the utilization of the diverter increases signal coupling between the communication device and the reader and/or charging device by about 10 times above those systems which do not utilize a diverter. Similarly, it is believed that the utilization of a repeater in a system increases the signal coupling between the communication device and the reader and/or charging device by about 20 percent to about 30 percent. Also, based on the embodiments described herein, it may be possible to achieve wireless charging of batteries without their removal from the housing/case in which they reside.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An object having a signal communication device, the object having an outer surface, the object further comprising:
   an RFID tag positioned on the outer surface of the object, the RFID tag having a resonant frequency and an antenna; and
   at least one passive repeater having a resonant frequency which is the same as that of the RFID tag, the at least one passive repeater being positioned on the outer surface of the object adjacent to the RFID tag such that signal coupling between the RFID tag and a reader is increased by greater than about 10 percent; wherein the RFID tag extends over greater than about 10 percent of the periphery of the object in cross section.

2. The object of claim 1, wherein the at least one passive repeater does not physically contact the antenna.

3. The object of claim 1, wherein the outer surface is cylindrical and the RFID tag conforms to the outer surface.

4. The object of claim 3, wherein the at least one passive repeater conforms to the outer surface of the object.

5. The object of claim 3, wherein the at least one passive repeater is a second RFID tag.

6. The object of claim 1, further comprising a second passive repeater.

7. The object of claim 6, wherein the second passive repeater is an RFID tag.

8. The object of claim 1, further comprising a plurality of RFID tags and a plurality of passive repeaters.

9. The object of claim 1, further comprising a plurality of passive repeaters.

10. The object of claim 1, further comprising a spaced passive repeater disposed adjacent to the outer surface of the object.

11. The object of claim 10, wherein the spaced passive repeater is an RFID tag.

12. The object of claim 1, wherein a gap exists between the at least one passive repeater and the RFID tag.

13. The object of claim 12, wherein the gap is between about 1 mm to about 75 mm.

14. The object of claim 12, wherein the gap is between about 10 mm to about 50 mm.

15. The object of claim 12, wherein the gap is between about 30 mm to about 50 mm.

16. The object of claim 1, wherein the at least one passive repeater increases signal coupling by between about 20 percent to about 100 percent.

17. The object of claim 1, wherein the at least one passive repeater increases signal coupling by between about 30 percent and about 90 percent.

18. The object of claim 1, wherein the at least one passive repeater increases signal coupling by between about 40 percent to about 80 percent.

19. The object of claim 1, wherein the at least one passive repeater increases signal coupling by greater than about 80 percent.

20. The object of claim 1, wherein the RFID tag extends over between about 10 percent to about 80 percent of the periphery of the object in cross section.

21. The object of claim 1, wherein the RFID tag extends over between about 20 percent to about 60 percent of the periphery of the object in cross section.

22. The object of claim 1, wherein the at least one passive repeater extends over between about 10 percent to about 80 percent of the periphery of the object in cross section.

23. The object of claim 1, wherein the object is a disposable or a rechargeable battery.

24. The object of claim 23, wherein the RFID tag provides data to the reader regarding remaining power level in the battery.

25. The object of claim 23, wherein the RFID tag provides data regarding the history of the battery.

* * * * *